United States Patent
Siebenhaar et al.

(10) Patent No.: US 9,731,058 B2
(45) Date of Patent: Aug. 15, 2017

(54) START-UP ALGORITHM FOR AN IMPLANTABLE BLOOD PUMP

(71) Applicant: Thoratec Corporation, Pleasanton, CA (US)

(72) Inventors: Andre Siebenhaar, Gipf-Oberfrick (CH); Andreas Fleischli, Zug (CH)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 15/219,578

(22) Filed: Jul. 26, 2016

(65) Prior Publication Data

US 2016/0331881 A1 Nov. 17, 2016

Related U.S. Application Data

(62) Division of application No. 14/014,957, filed on Aug. 30, 2013, now Pat. No. 9,427,510.

(Continued)

(51) Int. Cl.
*A61M 1/00* (2006.01)
*A61M 1/12* (2006.01)
(Continued)

(52) U.S. Cl.
CPC .......... *A61M 1/127* (2013.01); *A61M 1/1015* (2014.02); *A61M 1/1029* (2014.02); *A61M 1/1036* (2014.02); *F04D 1/00* (2013.01); *F04D 7/02* (2013.01); *F04D 13/024* (2013.01); *F04D 15/00* (2013.01); *F04D 29/426* (2013.01); *A61M 1/1031* (2014.02); *F04C 2270/0421* (2013.01);
(Continued)

(58) Field of Classification Search
CPC ............................ A61M 1/127; A61M 1/1015

USPC ....................................... 600/16; 417/423.12
See application file for complete search history.

(56) References Cited

U.S. PATENT DOCUMENTS

| 845,816 A | 3/1907 | Prindle |
| 888,654 A | 5/1908 | Prindle |

(Continued)

FOREIGN PATENT DOCUMENTS

| CN | 300837668 | 10/2008 |
| EP | 150320 | 5/1990 |

(Continued)

OTHER PUBLICATIONS

Barletta et al., "Design of a bearing less blood pump", Proc.3rd Int. Symp. on Magnetic Suspension Technology, Dec. 13-15, 1995, pp. 265-274.

*Primary Examiner* — Nadia A Mahmood
(74) *Attorney, Agent, or Firm* — Kilpatrick Townsend & Stockton LLP

(57) ABSTRACT

A system and a method for starting a rotor of an implantable blood pump are described. For example, a blood pump system includes a rotary motor having a stator and a rotor. The rotor has permanent magnetic poles for magnetic levitation of the rotor, and the stator has a plurality of pole pieces arranged circumferentially at intervals. The blood pump system includes a controller configured to control a start phase of the rotor, wherein the start phase is prior to the rotor being positioned in a predefined geometric volume for pumping blood and wherein the start phase includes performing a rotation of the rotor by an angle larger than an angle corresponding to a quarter of an angular distance between two neighboring magnetic poles of the rotor.

10 Claims, 9 Drawing Sheets

Related U.S. Application Data

(60) Provisional application No. 61/695,469, filed on Aug. 31, 2012.

(51) Int. Cl.
| | | |
|---|---|---|
| *A61M 1/10* | (2006.01) | |
| *F04D 1/00* | (2006.01) | |
| *F04D 7/02* | (2006.01) | |
| *F04D 13/02* | (2006.01) | |
| *F04D 15/00* | (2006.01) | |
| *F04D 29/42* | (2006.01) | |

(52) U.S. Cl.
CPC ....... *F05B 2240/14* (2013.01); *F05B 2240/30* (2013.01); *F05B 2270/10* (2013.01); *F05B 2270/404* (2013.01)

(56) References Cited

U.S. PATENT DOCUMENTS

| | | |
|---|---|---|
| 1,026,101 A | 5/1912 | Marsh |
| 2,128,988 A | 9/1938 | Christian |
| 2,747,512 A | 5/1956 | Fouche |
| 2,864,552 A | 12/1958 | Anderson et al. |
| 3,005,117 A | 10/1961 | Buchhold |
| 3,066,849 A | 12/1962 | Beams et al. |
| 3,122,101 A | 2/1964 | Baker et al. |
| 3,225,608 A | 12/1965 | Simon et al. |
| 3,401,640 A | 9/1968 | Fowler et al. |
| 3,499,274 A | 3/1970 | Fergason |
| 3,575,536 A | 4/1971 | Jacobs et al. |
| 3,597,022 A | 8/1971 | Waldron |
| 3,608,088 A | 9/1971 | Dorman et al. |
| 3,611,815 A | 10/1971 | Fischell et al. |
| 3,647,324 A | 3/1972 | Rafferty et al. |
| 3,650,581 A | 3/1972 | Boden et al. |
| 3,938,913 A | 2/1976 | Isenberg et al. |
| 3,957,389 A | 5/1976 | Rafferty et al. |
| 4,082,376 A | 4/1978 | Wehde et al. |
| 4,135,253 A | 1/1979 | Reich et al. |
| 4,167,296 A | 9/1979 | Dendy |
| 4,213,207 A | 7/1980 | Wilson et al. |
| 4,340,260 A | 7/1982 | Forster et al. |
| 4,382,199 A | 5/1983 | Isaacson |
| 4,398,773 A | 8/1983 | Boden et al. |
| 4,405,286 A | 9/1983 | Studer |
| 4,408,966 A | 10/1983 | Maruyama et al. |
| 4,475,866 A | 10/1984 | Kambe et al. |
| 4,507,048 A | 3/1985 | Belenger et al. |
| 4,589,822 A | 5/1986 | Clausen et al. |
| 4,598,697 A | 7/1986 | Numazawa et al. |
| 4,642,036 A | 2/1987 | Young et al. |
| 4,688,998 A | 8/1987 | Olsen et al. |
| 4,704,121 A | 11/1987 | Moise et al. |
| 4,763,032 A | 8/1988 | Bramm et al. |
| 4,779,614 A | 10/1988 | Moise |
| 4,844,707 A | 7/1989 | Kletschka et al. |
| 4,876,492 A | 10/1989 | Lester et al. |
| 4,878,831 A | 11/1989 | Ewing et al. |
| 4,898,759 A | 2/1990 | Hoover et al. |
| 4,929,158 A | 5/1990 | Girault |
| 4,944,748 A | 7/1990 | Bramm et al. |
| 4,957,504 A | 9/1990 | Chardack |
| 5,055,005 A | 10/1991 | Kletschka |
| 5,078,741 A | 1/1992 | Bramm et al. |
| 5,106,273 A | 4/1992 | Lemarquand et al. |
| 5,112,200 A | 5/1992 | Isaacson et al. |
| 5,112,202 A | 5/1992 | Oshima et al. |
| 5,126,612 A | 6/1992 | Girault |
| 5,127,792 A | 7/1992 | Katsuta et al. |
| 5,159,219 A | 10/1992 | Chu et al. |
| 5,177,387 A | 1/1993 | McMichael et al. |
| 5,195,877 A | 3/1993 | Kletschka |
| 5,220,232 A | 6/1993 | Rigney, II et al. |
| 5,341,059 A | 8/1994 | Fujimoto et al. |
| 5,385,581 A | 1/1995 | Bramm et al. |
| 5,470,208 A | 11/1995 | Kletschka |
| 5,708,346 A | 1/1998 | Schob |
| 5,725,357 A | 3/1998 | Nakazeki et al. |
| 5,798,454 A | 8/1998 | Nakazeki et al. |
| 5,808,437 A | 9/1998 | Schoeb |
| 5,917,297 A | 6/1999 | Gerster et al. |
| 5,928,131 A | 7/1999 | Prem |
| 5,947,703 A | 9/1999 | Nojiri et al. |
| 6,023,115 A | 2/2000 | Maejima |
| 6,053,705 A | 4/2000 | Schoeb et al. |
| 6,100,618 A | 8/2000 | Schoeb et al. |
| 6,121,704 A | 9/2000 | Fukuyama et al. |
| 6,130,494 A | 10/2000 | Schoeb |
| 6,146,325 A | 11/2000 | Lewis et al. |
| 6,191,513 B1 | 2/2001 | Chen et al. |
| 6,201,329 B1 | 3/2001 | Chen |
| 6,222,290 B1 | 4/2001 | Schöb et al. |
| 6,227,797 B1 | 5/2001 | Watterson et al. |
| 6,232,687 B1 | 5/2001 | Hollenbeck et al. |
| 6,234,772 B1 | 5/2001 | Wampler et al. |
| 6,249,067 B1 | 6/2001 | Schob et al. |
| 6,259,179 B1 | 7/2001 | Fukuyama et al. |
| 6,264,635 B1 | 7/2001 | Wampler et al. |
| 6,278,251 B1 | 8/2001 | Schöb |
| 6,293,901 B1 | 9/2001 | Prem |
| 6,302,661 B1 | 10/2001 | Khanwilkar et al. |
| 6,348,752 B1 | 2/2002 | Molnar et al. |
| 6,351,048 B1 | 2/2002 | Schob et al. |
| 6,355,998 B1 | 3/2002 | Schöb et al. |
| 6,394,769 B1 | 5/2002 | Bearnson et al. |
| 6,447,266 B2 | 9/2002 | Antaki et al. |
| 6,468,041 B2 | 10/2002 | Ozaki |
| 6,559,567 B2 | 5/2003 | Schöb |
| 6,575,717 B2 | 6/2003 | Ozaki et al. |
| 6,589,030 B2 | 7/2003 | Ozaki |
| 6,605,032 B2 | 8/2003 | Benkowski et al. |
| 6,623,475 B1 | 9/2003 | Siess |
| 6,626,644 B2 | 9/2003 | Ozaki |
| 6,634,224 B1 | 10/2003 | Schöb et al. |
| 6,640,617 B2 | 11/2003 | Schöb et al. |
| 6,688,861 B2 | 2/2004 | Wampler |
| 6,707,200 B2 | 3/2004 | Carroll et al. |
| 6,711,943 B1 | 3/2004 | Schöb et al. |
| 6,717,311 B2 | 4/2004 | Locke |
| 6,817,836 B2 | 11/2004 | Nose et al. |
| 6,879,074 B2 | 4/2005 | Amrhein et al. |
| 6,949,066 B2 | 9/2005 | Bearnson et al. |
| 7,070,398 B2 | 7/2006 | Olsen et al. |
| 7,112,903 B1 | 9/2006 | Schob |
| 7,138,776 B1 | 11/2006 | Gauthier et al. |
| 7,150,711 B2 | 12/2006 | Nüsser et al. |
| D534,548 S | 1/2007 | Urano et al. |
| 7,160,242 B2 | 1/2007 | Yanai |
| 7,229,258 B2 | 6/2007 | Wood et al. |
| 7,229,474 B2 | 6/2007 | Hoffmann et al. |
| 7,239,098 B2 | 7/2007 | Masino |
| 7,284,956 B2 | 10/2007 | Nose et al. |
| 7,338,521 B2 | 3/2008 | Antaki et al. |
| 7,462,019 B1 | 12/2008 | Allarie et al. |
| 7,497,116 B2 | 3/2009 | Miyakoshi et al. |
| 7,511,443 B2 | 3/2009 | Townsend et al. |
| 7,578,782 B2 | 8/2009 | Miles et al. |
| 7,591,777 B2 | 9/2009 | LaRose et al. |
| 7,645,225 B2 | 1/2010 | Medvedev et al. |
| 7,699,588 B2 | 4/2010 | Mendler |
| 7,854,631 B2 | 12/2010 | Townsendl et al. |
| 7,861,582 B2 | 1/2011 | Miyakoshi et al. |
| 7,887,479 B2 | 2/2011 | LaRose et al. |
| 7,951,062 B2 | 5/2011 | Morello |
| 7,976,271 B2 | 7/2011 | LaRose et al. |
| 8,152,493 B2 | 4/2012 | Thyagarajan et al. |
| 8,157,720 B2 | 4/2012 | Marseille et al. |
| 8,303,482 B2 | 11/2012 | Schima et al. |
| 8,382,830 B2 | 2/2013 | Maher et al. |
| 8,506,470 B2 | 8/2013 | Larose et al. |
| 8,517,699 B2 | 8/2013 | Horvath |
| 8,556,625 B2 | 10/2013 | Bolyard et al. |
| 8,597,350 B2 | 12/2013 | Rudser et al. |

(56) References Cited

U.S. PATENT DOCUMENTS

| | | |
|---|---|---|
| 8,764,621 B2 | 7/2014 | Badstibner et al. |
| 8,870,739 B2 | 10/2014 | Larose et al. |
| 8,882,477 B2 | 11/2014 | Fritz, IV et al. |
| 8,956,275 B2 | 2/2015 | Bolyard et al. |
| 9,091,271 B2 | 7/2015 | Bourque |
| 2002/0094281 A1 | 7/2002 | Khanwilkar et al. |
| 2004/0236420 A1 | 11/2004 | Yamane et al. |
| 2005/0004421 A1 | 1/2005 | Pacella et al. |
| 2005/0135948 A1 | 6/2005 | Olsen et al. |
| 2005/0147512 A1 | 7/2005 | Chen et al. |
| 2006/0127227 A1 | 6/2006 | Mehlhorn et al. |
| 2007/0100196 A1 | 5/2007 | LaRose et al. |
| 2009/0064755 A1 | 3/2009 | Fleischli et al. |
| 2009/0234447 A1 | 9/2009 | LaRose et al. |
| 2010/0130809 A1 | 5/2010 | Morello |
| 2010/0150749 A1 | 6/2010 | Horvath |
| 2010/0152526 A1 | 6/2010 | Pacella et al. |
| 2010/0241223 A1 | 9/2010 | Lee et al. |
| 2010/0327687 A1 | 12/2010 | Iannello et al. |
| 2011/0002794 A1 | 1/2011 | Haefliger et al. |
| 2011/0031836 A1 | 2/2011 | Nussbaumer |
| 2011/0054239 A1 | 3/2011 | Sutton et al. |
| 2011/0071337 A1 | 3/2011 | Thompson et al. |
| 2011/0144413 A1 | 6/2011 | Foster |
| 2011/0144744 A1 | 6/2011 | Wampler |
| 2011/0187217 A1 | 8/2011 | Nussbaumer |
| 2011/0237863 A1 | 9/2011 | Ricci et al. |
| 2011/0245582 A1 | 10/2011 | Zafirelis et al. |
| 2011/0313237 A1 | 12/2011 | Miyakoshi et al. |
| 2012/0003108 A1 | 1/2012 | Ozaki et al. |
| 2012/0035411 A1 | 2/2012 | LaRose et al. |
| 2012/0046514 A1* | 2/2012 | Bourque .............. A61M 1/101 600/16 |
| 2012/0059212 A1 | 3/2012 | LaRose et al. |
| 2012/0134832 A1 | 5/2012 | Wu |
| 2012/0226097 A1 | 9/2012 | Smith et al. |
| 2012/0245681 A1 | 9/2012 | Casas et al. |
| 2012/0253103 A1 | 10/2012 | Robert |
| 2012/0310036 A1 | 12/2012 | Peters et al. |
| 2013/0164161 A1 | 6/2013 | Schöb |
| 2013/0331934 A1 | 12/2013 | Kabir et al. |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |

FOREIGN PATENT DOCUMENTS

| | | |
|---|---|---|
| EP | 60569 | 12/1990 |
| EP | 378251 | 6/1994 |
| EP | 2357374 | 8/2011 |
| GB | 1491710 | 11/1977 |
| JP | 01257792 | 10/1989 |
| JP | 02016390 | 1/1990 |
| JP | D1373017 | 10/2009 |
| TW | D136032 | 7/2010 |
| WO | 9729795 | 8/1997 |
| WO | 9953974 | 10/1999 |
| WO | 2010036815 | 4/2010 |
| WO | 2012028181 | 3/2012 |
| WO | 2012040551 | 3/2012 |
| WO | 2014036410 | 3/2014 |

\* cited by examiner

US 9,731,058 B2

START-UP ALGORITHM FOR AN IMPLANTABLE BLOOD PUMP

CROSS-REFERENCES TO RELATED APPLICATIONS

This application is a divisional of U.S. application Ser. No. 14/014,957, filed Aug. 30, 2013, which application claims the benefit U.S. Provisional Application No. 61/695,469, filed Aug. 31, 2912, the entire contents of which are incorporated herein by reference for all purposes.

The description relates to U.S. Pat. No. 9,091,271, issued Jul. 28, 2015, and titled "Implantable Blood Pump," the entire contents of which are incorporated herein for all purposes by reference.

FIELD

This description relates to motor control, and in various aspects a start-up algorithm, for an implantable blood pump.

BACKGROUND

Ventricular assist devices, known as VADs, are implantable blood pumps used for both short-term and long-term applications where a patient's heart is incapable of providing adequate circulation. For example, a patient suffering from heart failure may use a VAD while awaiting a heart transplant. In another example, a patient may use a VAD while recovering from heart surgery. Thus, a VAD can supplement a weak heart or can effectively replace the natural heart's function. VADs can be implanted in the patient's body and powered by an electrical power source inside or outside the patient's body.

Some implantable blood pumps employ rotor designs where the rotor needs to be released from magnetic attraction before the rotor can be activated by a motor. For such starting algorithms of a rotor in an implantable blood pump, significant currents are required that require heavyweight, expensive, and/or bulky power supplies.

BRIEF SUMMARY

The present disclosure describes one or more general aspects, implementations or embodiments involving devices, systems and computer-implemented methods for a start-up algorithm for an implantable blood pump.

One or more of the following aspects of this disclosure can be embodied as methods that include the corresponding actions. One or more of the following aspects of this disclosure can be implemented in a device comprising a processor, a processor-readable medium coupled to the processor having instructions stored thereon which, when executed by the processor, cause the processor to perform operations according to the one or more of the following aspects. One or more of the following aspects of this disclosure can be implemented on a computer-readable medium having instructions stored thereon that, when executed by a processor, cause the processor to perform operations according to the one or more of the following aspects.

In aspect 1, a blood pump system comprises: a rotary motor comprising a stator and a rotor, the rotor having a predefined number of permanent magnetic poles for magnetic levitation of the rotor, the stator having a plurality of pole pieces arranged circumferentially at intervals; and a controller configured to control a start phase of the rotor, wherein the start phase is prior to the rotor being positioned in a predefined geometric volume for pumping blood and wherein the start phase includes performing a rotation of the rotor by an angle larger than an angle corresponding to a quarter of an angular distance between two neighboring magnetic poles of the rotor.

The predefined geometric volume denotes a volume for the rotor in which the rotor is operable to pump blood and to rotate freely in a levitated position. When being within the predefined geometric volume, the rotor does not contact any wall or parts of adjacent walls. A distance between parts of the rotor and adjacent walls may also be sufficiently large to prevent harm to the blood while pumping.

Aspect 2 according to aspect 1, wherein the angle of the rotation is a multiple of about half of the angular distance between two neighboring magnetic poles of the rotor.

Aspect 3 according to aspect 1, wherein the angle of the rotation is about half of the angular distance between two neighboring magnetic poles of the rotor.

Aspect 4 according to aspect 1, wherein the predefined number of magnetic poles of the rotor is two, four or eight or a multiple thereof.

Aspect 5 according to aspect 1, wherein the angle of the rotation is between about 45 and about 270 degrees.

Aspect 6 according to aspect 1, wherein the angle of the rotation is about 90 degrees or about 270 degrees.

Aspect 7 according to aspect 1, wherein the rotation corresponds substantially to an angle of twice the interval between two neighboring pole pieces of the stator.

Aspect 8 according to any one of aspects 1 to 7, wherein the blood pump system comprises an implantable blood pump housing, wherein the rotary motor and the controller are positioned within the implantable blood pump housing.

In aspect 9, a blood pump system comprises: a rotary motor comprising a stator and a rotor, the rotor having a predefined number of permanent magnetic poles for magnetic levitation of the rotor; and a controller configured to control a start phase of the rotor, wherein the start phase is prior to the rotor being positioned in a predefined geometric volume for pumping blood and wherein the start phase includes rolling the rotor from a start position to a target position, wherein a magnet of the rotor experiences a reduced magnetic attraction at the target position compared to the start position.

Aspect 10 according to aspect 9, wherein the stator comprises a plurality of pole pieces arranged circumferentially at intervals; and wherein the start phase includes performing a rotation of the rotor by an angle larger than an angle corresponding to a quarter of an angular distance between two neighboring magnetic poles of the rotor.

Aspect 11 according to aspect 10, wherein the angle of the rotation is about half of the angular distance between two neighboring magnetic poles of the rotor Aspect 12 according to any one of aspects 1 to 11, wherein the predefined geometric volume defines a volume for the rotor in which the rotor is operable to pump blood and to rotate freely in a levitated position.

Aspect 13 according to any one of aspects 1 to 12, further comprising: one or more Hall sensors for determining a current position of the rotor; and the controller further adapted to perform a take-off operation attempting to move the rotor into the predefined geometric volume, and to determine if the rotor is positioned within the predefined geometric volume after performing the take-off operation.

Aspect 14 according to aspect 13, wherein the controller further adapted to determine if the rotor is positioned within the predefined geometric volume and if the rotor is not positioned within the predefined geometric volume to perform the additional operations of: performing a second rotation of the rotor corresponding substantially to an angle of twice the interval between two neighboring pole pieces of the stator; and of rolling the rotor from a second start position to a second target position, wherein the magnet of the rotor experiences a reduced magnetic attraction at the second target position compared to the second start position; and of performing a second take-off operation attempting to move the rotor into the predefined geometric volume.

Aspect 15 according to any of aspects 1 to 14, wherein the controller is further adapted to rotate the rotor within the predefined geometric volume.

In aspect 16 a method for starting a rotor of an implantable blood pump comprises:

performing an initial rotation of the rotor by an angle larger than an angle corresponding to a quarter of an angular distance between two neighboring magnetic poles of the rotor.

Aspect 17 according to aspect 16, wherein the angle of the rotation is a multiple of about half of the angular distance between two neighboring magnetic poles of the rotor.

Aspect 18 according to aspect 16, wherein the angle of the rotation is about half of the angular distance between two neighboring magnetic poles of the rotor.

Aspect 19 according to aspect 16, wherein the predefined number of magnetic poles of the rotor is two, four or eight or a multiple thereof.

Aspect 20 according to aspect 16, wherein the angle of the initial rotation is between about 45 and about 270 degrees.

Aspect 21 according to aspect 16, wherein the angle of the initial rotation is about 90 degrees.

In aspect 22, a method for starting a rotor of an implantable blood pump comprises: rolling the rotor from a start position to a target position prior to pumping blood, wherein a magnet of the rotor experiences a reduced magnetic attraction at the target position compared to the start position.

Aspect 23 according to aspect 22, wherein an equator of the magnet is in physical contact with the target position after the rolling of the rotor or wherein the equator of the magnet is in a proximity of the target position after the rolling of the rotor.

In aspect 24 a method for starting a rotor of an implantable blood pump comprises: performing an initial rotation of the rotor by an angle larger than an angle corresponding to a quarter of an angular distance between two neighboring magnetic poles of the rotor; and rolling the rotor from a first start position to a first target position prior to pumping blood, wherein a magnet of the rotor experiences a reduced magnetic attraction at the first target position compared to the first start position.

Aspect 25 according to aspect 24, wherein the angle of the rotation is about half of the angular distance between two neighboring magnetic poles of the rotor or a multiple thereof.

Aspect 26 according to aspect 24, wherein the angle of the initial rotation is between about 45 and about 270 degrees.

Aspect 27 according to aspect 24, wherein the angle of the initial rotation is about 90 degrees.

Aspect 28 according to aspect 24, wherein a current required to start the rotor is less than about 5 ampere.

Aspect 29 according to any one of aspects 24 to 28, further comprising: determining a current position of the rotor by using one or more Hall sensors; perform a take-off operation attempting to move the rotor into the predefined geometric volume, and determine if the rotor is positioned within the predefined geometric volume after performing the take-off operation.

Aspect 30 according to aspect 29, further comprising: determine if the rotor is positioned within the predefined geometric volume and if the rotor is not positioned within the predefined geometric volume to perform the additional operations of: performing a second rotation of the rotor corresponding substantially to an angle of twice the interval between two neighboring pole pieces of the stator; and rolling the rotor from a second start position to a second target position, wherein the magnet of the rotor experiences a reduced magnetic attraction at the second target position compared to the second start position; and performing a second take-off operation attempting to move the rotor into the predefined geometric volume.

Aspect 31 according to aspect 29 or 30, further comprising accelerating the rotor if the rotor is positioned within the predefined geometric volume within the pump.

Aspect 32 according to any of aspects 16 to 31, further comprising rotating the rotor within the predefined geometric volume, wherein the rotating is preferably controlled by a controller.

In aspect 33, a computer-readable medium having computer-executable instructions stored thereon that, when executed by a processor, cause the processor to perform operations comprises: performing an initial rotation of the rotor by an angle of between 45 and 270 degrees prior to pumping blood; rolling the rotor from a first start position to a first target position prior to pumping blood, wherein a magnet of the rotor experiences a reduced magnetic attraction at the first target position compared to the first start position.

Aspect 34 according aspect 33, wherein the angle is preferentially 90 degrees.

Aspect 35 according aspect 33 or 34, wherein a current required to start the rotor is less than about 5 ampere.

Aspect 36 according to any of aspects 33 to 35, further having computer-executable instructions stored thereon that, when executed by a processor, cause the processor to perform operations, comprising: determining a current position of the rotor by using one or more Hall sensors; and perform a take-off operation attempting to move the rotor into the predefined geometric volume, and determine if the rotor is positioned within the predefined geometric volume after performing the take-off operation.

Aspect 37 according aspect 36, further having computer-executable instructions stored thereon that, when executed by a processor, cause the processor to perform operations, comprising: determine if the rotor is positioned within the predefined geometric volume and if the rotor is not positioned within the predefined geometric volume to perform the additional operations of: performing a second rotation of the rotor corresponding substantially to an angle of twice the interval between two neighboring pole pieces of the stator; and rolling the rotor from a second start position to a second target position, wherein the magnet of the rotor experiences a reduced magnetic attraction at the second target position compared to the second start position;

and performing a second take-off operation attempting to move the rotor into the predefined geometric volume.

Aspect 38 according to aspect 36 or 37, further comprising: accelerating the rotor if the rotor is positioned within the predefined geometric volume within the pump.

The following general aspects may be combinable with any one of the aspects 1 to 38.

In one general aspect, an implantable blood pump includes a housing and a blood flow conduit. Within the housing, the blood pump includes a stator located about the blood flow conduit and a magnetically-levitated rotor.

In another general aspect, an implantable blood pump includes a housing defining an inlet opening and an outlet opening. Within the housing, a dividing wall defines a blood flow conduit extending between the inlet opening and the outlet opening of the housing. The blood pump has a rotary motor that includes a stator and a rotor. The stator is disposed within the housing circumferentially about the dividing wall such that the inner blood flow conduit extends through the stator.

In another general aspect, an implantable blood pump includes a puck-shaped housing having a first face defining an inlet opening, a peripheral sidewall, and a second face opposing the first face. The blood pump has an internal dividing wall defining an inner blood flow conduit extending between the inlet opening and an outlet opening of the housing. The puck-shaped housing has a thickness from the first face to the second face that is less than a width of the housing between opposing portions of the peripheral sidewall. The blood pump also has a motor having a stator and a rotor. The stator is disposed in the housing circumferentially about the blood flow conduit and includes magnetic levitation components operable to control an axial position and a radial position of the rotor. The rotor is disposed in the inner blood flow conduit and includes an impeller operable to pump blood from the inlet opening to the outlet opening through at least a portion of the magnetic levitation components of the stator.

Implementations of the above aspects may include one or more of the following features. For example, the stator is disposed circumferentially about at least a part of the rotor and is positioned relative to the rotor such that in use blood flows within the blood flow conduit through the stator before reaching the rotor. The rotor has permanent magnetic poles for magnetic levitation of the rotor. A passive magnetic control system is configured to control an axial position of the rotor relative to the stator, and an active electromagnetic control system is configured to radially center the rotor within the inner blood flow conduit. An electromagnetic control system controls at least one of a radial position and an axial position of the rotor relative to the stator, and the electromagnetic control system has control electronics located within the housing about the dividing wall.

The control electronics are located between the inlet opening and the stator. The control electronics can be configured to control the active magnetic control system. The rotor has only one magnetic moment. The stator includes a first coil for driving the rotor and a second coil for controlling a radial position of the rotor, and the first coil and the second coil are wound around a first pole piece of the stator. The housing has a first face that defines the inlet opening, a second face opposing the first face, and a peripheral wall extending from the first face to the second face. The housing includes a rounded transition from the second face to the peripheral wall. The housing defines a volute located such that in use blood flows within the blood flow conduit through the stator before reaching the volute. The volute can be located between the stator and the second face. The housing can also include a cap that includes the second face, defines at least part of the volute, and defines at least part of the outlet. The cap is engaged with the peripheral wall of the housing. The housing also includes an inlet cannula extending from the first face and in fluid communication with the inlet opening. The inlet cannula can be inserted into the patient's heart. The outlet opening is defined in the second face and/or the peripheral wall. A thickness of the housing between the first face and the second face is less than a width of the housing.

In another general aspect, a method includes inserting a puck-shaped blood pump housing into a patient's body. The blood pump is inserted such that an opening defined in a first flat face of the housing that is proximate to a stator of the blood pump faces the patient's heart.

Additionally, the blood pump is inserted such that a second rounded face of the housing that is proximate to an impeller of the blood pump faces away from the patient's heart. The first face is disposed against a portion of the patient's heart such that the second face of the housing faces away from the heart of the patient. In some implementations, the method includes inserting an inlet cannula of the housing into the patient's heart.

In another general aspect, making a blood pump includes assembling a motor stator and control electronics in a puck-shaped housing circumferentially about an internal dividing wall. The internal dividing wall defines an inner blood flow conduit that extends from an inlet opening to an outlet opening of the housing. The stator is assembled in the housing such that the inner blood flow conduit extends through the motor stator. Disposed within the inner blood flow conduit is a magnetically-levitated rotor. The rotor is surrounded by the stator such that impeller blades carried by the rotor are downstream of the stator from the inlet opening. In use, the impeller pumps blood from the inlet opening to the outlet opening through the stator.

Implementations may include one or more of the following features. For example, the rotor has only one magnetic moment. The stator includes at least one first coil for driving the rotor and at least one second coil for controlling a radial position of the rotor, the at least one first coil and the at least one second coil being wound around a first pole piece of the stator. The housing includes a first face that defines the inlet opening, and further comprising engaging an end cap with a peripheral wall of the housing, the end cap including a second face, defining at least part of a volute, and defining at least part of the outlet opening. The housing includes a rounded transition from the second face to the peripheral wall. The housing further includes an inlet cannula extending from the first face and in fluid communication with the inlet opening. A thickness of the housing between the first face and the second face is less than a width of the housing.

In another general aspect, a method of pumping blood includes magnetically rotating a centrifugal pump impeller of a blood pump device to draw blood from a patient's heart through an inlet opening of a housing of the blood pump device into an inner blood flow conduit within a stator in the housing, through the inner blood flow conduit, and through an outlet opening of the housing. The method includes selectively controlling a radial position of the impeller within the inner blood flow conduit.

The details of one or more of these and other aspects, implementations or embodiments are set forth in the accompanying drawings and the description below. Other features, aims and advantages will be apparent from the description and drawings, and from the claims.

Figure 1:
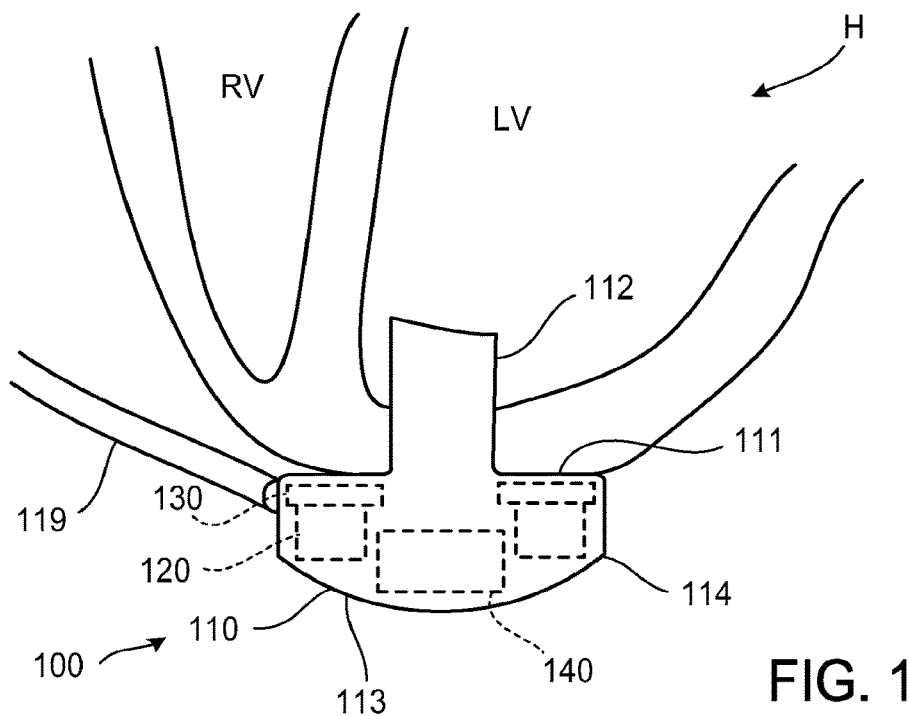
FIG. 1 is an illustration of a blood pump in a use position implanted in a patient's body.

Reference numbers and designations in the various drawings indicate exemplary aspects, implementations or embodiments of particular features of the present disclosure.

DETAILED DESCRIPTION

This description relates to a start-up algorithm for an implantable blood pump. Specifically, tools and computer-implemented methods for reducing the current demand of implantable blood pumps are described herein.

The subject matter described in this disclosure can be implemented in particular aspects or embodiments so as to realize one or more of the following advantages.

First, a current consumption of an implantable blood pump may be reduced. A peak current demanded by a start-up of an implantable blood pump may be reduced. This may prevent a reset of a power supply of an implantable blood pump due to an overload. For example, a peak current of less than 5 ampere may be achieved for the start-up.

Second, a current needed to perform a rolling of a magnet of a rotor of an implantable blood pump may be reduced. For example, a current of less than about 2 ampere may be achieved for the rolling of the magnet.

Third, improved positions for a successful start-up of the rotor may be provided for the magnet of the rotor. For example, no later than a second try of the start-up may be successful. Since each start-up attempt uses power, conventional techniques requiring many start-up attempts tend to be energy inefficient.

Fourth, a time duration needed for a successful start-up of a rotor of an implantable blood pump may be reduced. For example, the time duration may be reduced to less than 3 seconds.

Other advantages of this disclosure will be apparent to those skilled in the art.

With reference to FIGS. 1 to 5, a left ventricular assist blood pump 100 having a puck-shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2, 4, and 5, for example.

Figure 2:
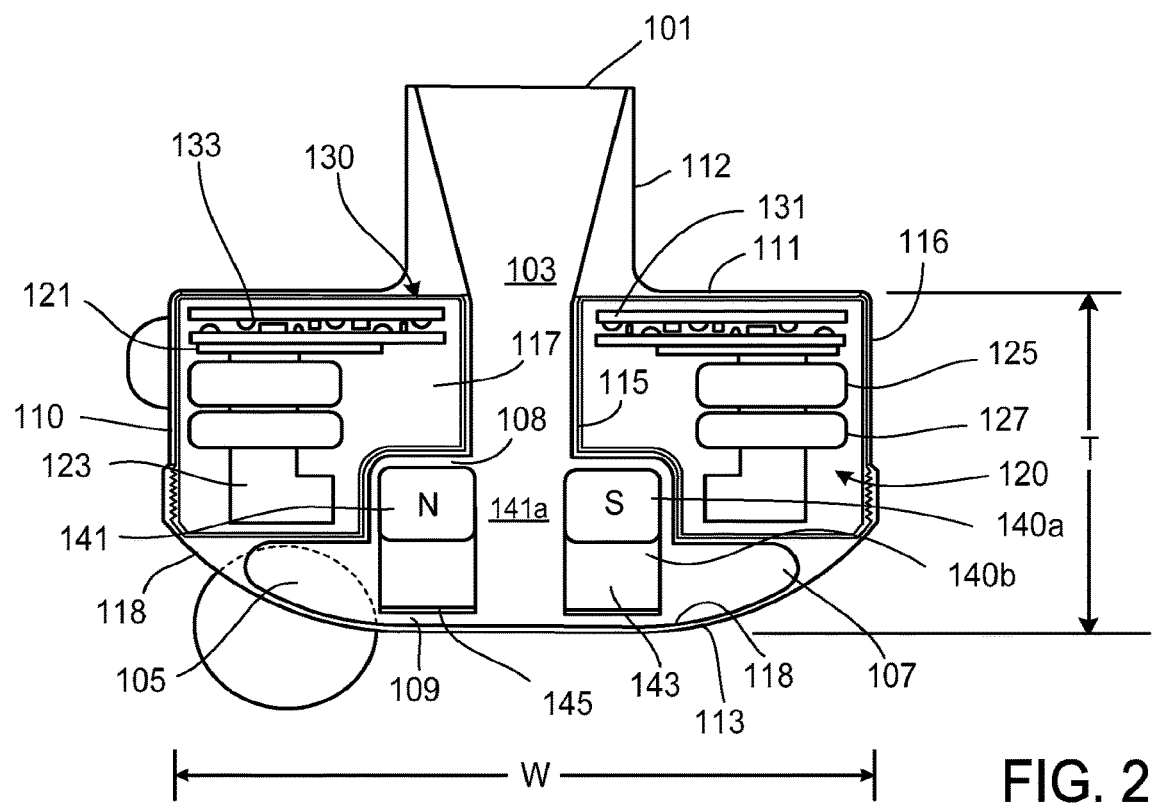
FIG. 2 is a cross-sectional view of the blood pump of FIG. 1.

Referring to FIG. 2, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

Figure 3:
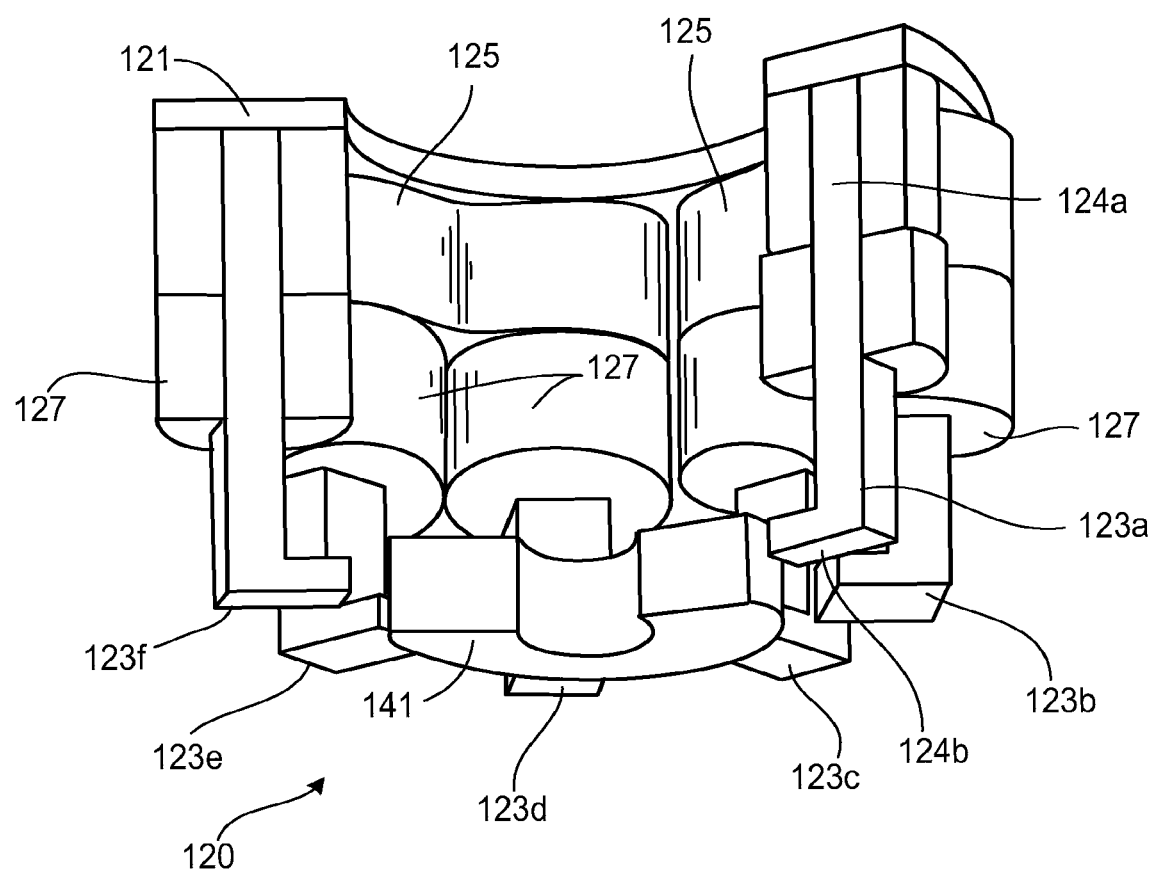
FIG. 3 is a partial cut-away perspective view of a stator of a blood pump.
Figure 4:
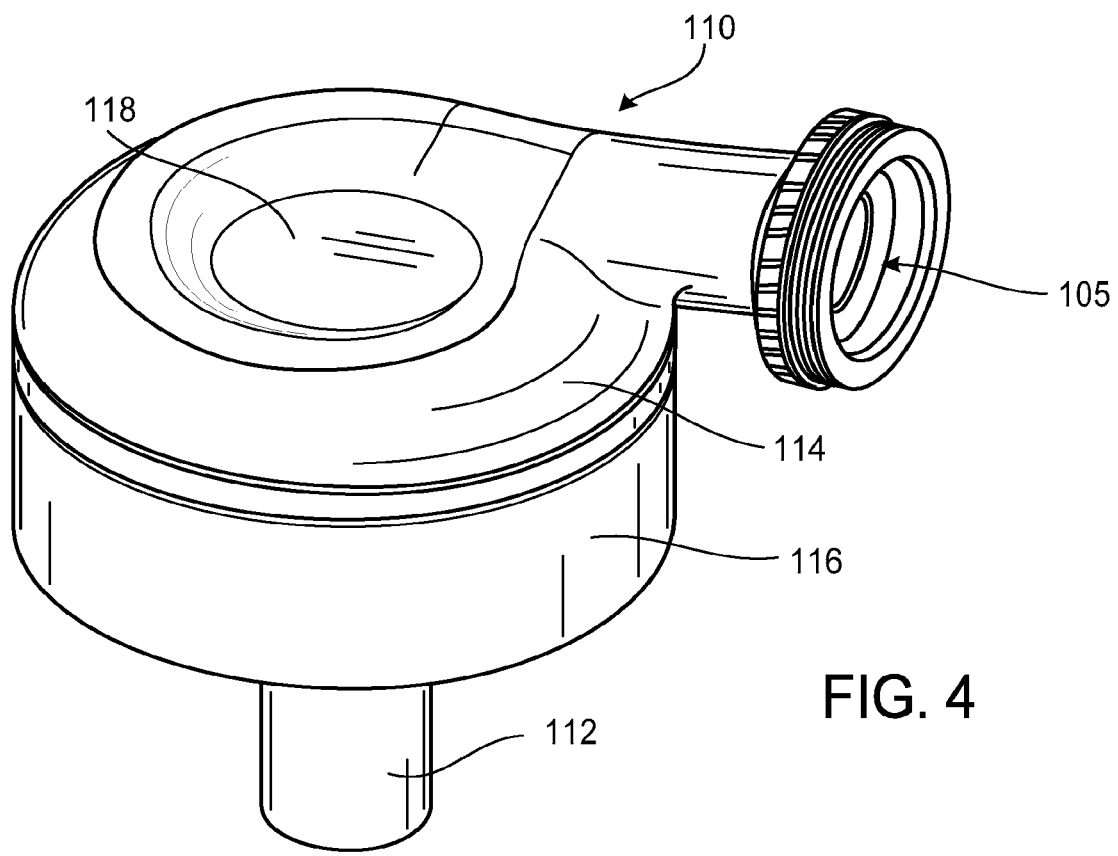
FIG. 4 is a bottom perspective view of a blood pump.
Figure 5:
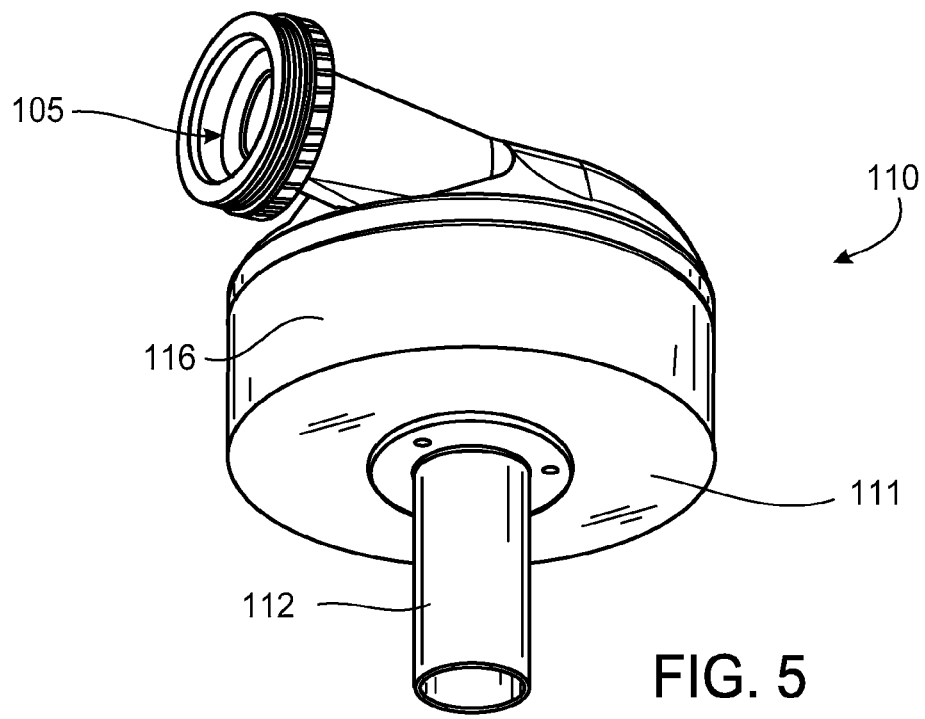
FIG. 5 is a top perspective view of the blood pump of FIG. 4.

With continued reference to FIG. 2 and with reference to FIG. 3, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein for all purposes by reference. The control electronics 130 and the stator 120 receive electrical power from a remote power supply via a cable 119 (FIG. 1). Further related patents, namely U.S. Pat. Nos. 5,708,346, 6,053,705, 6,100,618, 6,879,074, 7,112,903, 6,278,251, 6,278,251, 6,351,048, 6,249,067, 6,222,290, 6,355,998 and U.S. Pat. No. 6,634,224, are incorporated herein for all purposes by reference in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105.

Figure 6:
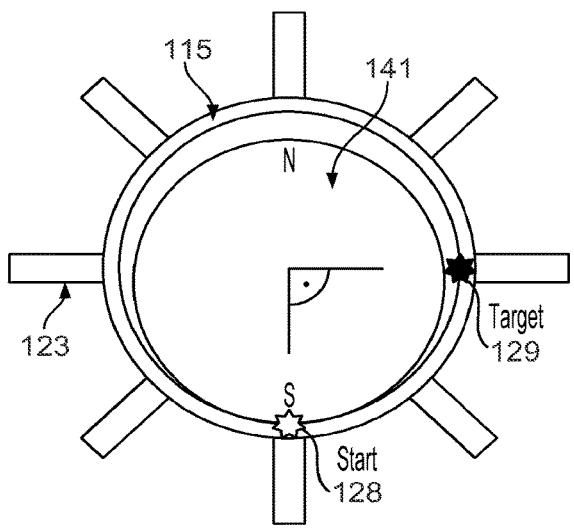
FIG. 6 describes a current consumption of a standard start-up that is successful in this example.
Figure 6:
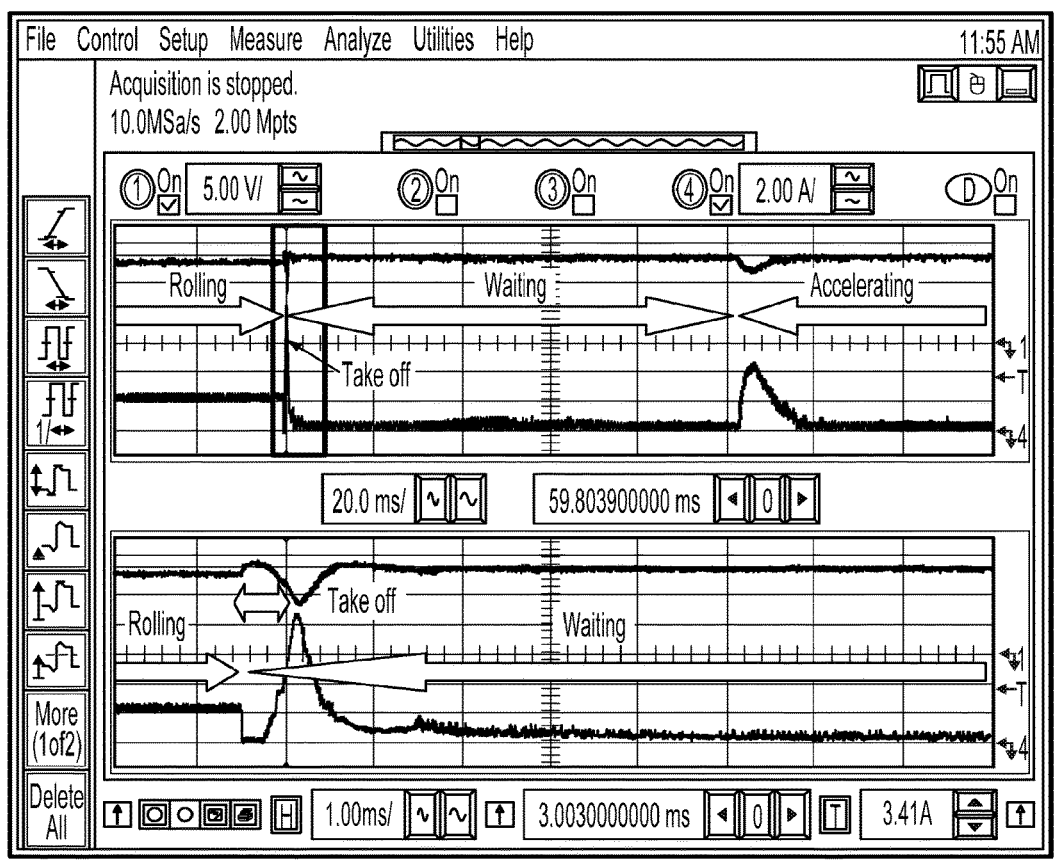

FIG. 6 describes a current consumption of a start-up procedure that is successful in this example. Start-up procedures may include a rolling phase, a take-off, a waiting phase and an accelerating phase. At the beginning of the start-up, the permanent magnet 141 is magnetically attracted by the pole pieces 123a-f and/or the coils 125, 127 of the stator 120. The magnet 141 may contact the wall 115 or one or more pole pieces 123 of the stator 120 at a start position 128. In the rolling phase the control electronics of the implantable blood pump 100 may roll the permanent magnet 141 of the rotor 140 along a wall 115 or along a stator 120 to reduce a magnetic attraction the magnet 141 experiences (e.g., due to the presence of one or more of the pole pieces 123a-123f and/or one or more of the coils 125, 127 of the stator). As a target of the rolling phase, the permanent magnet 141 of the rotor 140 is aligned in such a way that an equator of the magnet 141 faces or touches a target position 129, or the equator is touching the wall 115 at a proximity of one of the pole pieces 123a-f of the stator 120 after the rolling. This may lead to a reduced magnetic attracting force between the magnet 141 and the stator 120 (e.g., the pole pieces 123a-f) compared to the situation before the rolling. The part of the magnet 141 contacting the wall 115 or one or more pole pieces 123a-f of the stator 120 at the start position 128 is then, after rolling, located at a position between two pole pieces 123a-f of the stator 120, wherein the distance of the part from the nearest pole piece may be increased due to the rolling. In this context, it may also be the case that the rotor 140 does not touch the wall 115 with a part of a pole of the magnet 141 but with a part of the magnet not being one of the magnetic poles.

In an aspect, if the electronics of the pump provide sufficient current, a force may be applied to the magnet 141 to remove the magnet 141 from the wall 115 or the stator 120 during the take-off. After the take-off and the waiting phase, the rotor 140 is accelerated to the nominal rotation speed of the operational pump 100. FIG. 6 illustrates that the peak current during the take-off may exceed the peak current during the accelerating phase.

Figure 7:
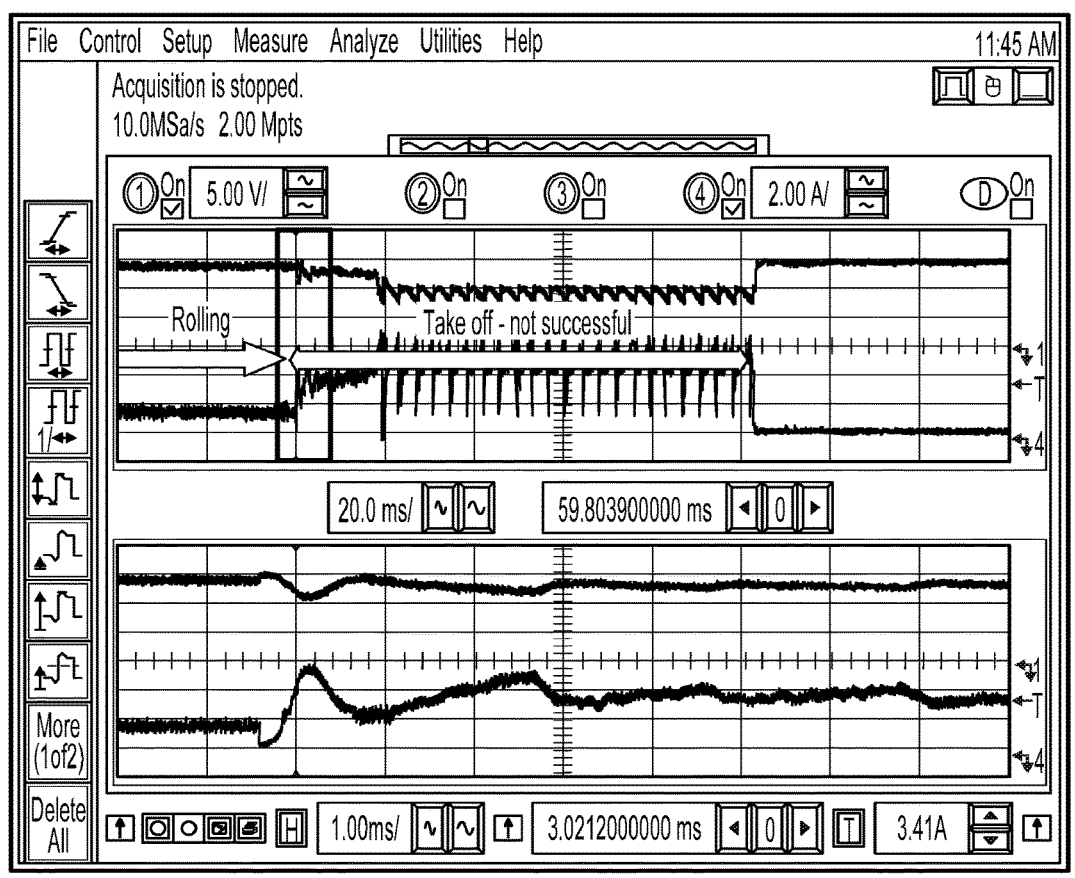
FIG. 7 describes a current consumption of a standard start-up that fails in this example.

FIG. 7 describes a current consumption of a standard start-up that fails in this example. In this example, the initial take-off is not successful and subsequent attempts are performed to repeat the whole start-up algorithm or the take-off. This may lead to repeatedly applying the peak current of the take-off to the pump 100 which may eventually lead to a breakdown of the power supply due to overload. A reset of the power supply may be a consequence. In situations, where the magnet 141 of the rotor 140 is stuck at the wall 115 and prevents a successful start-up of the rotor 140, the electrical current demand for a successful start-up may be too high for the power supply. In this situation, the implantable blood pump 100 may not be able to start pumping blood through the flow conduit 103.

Figure 8:
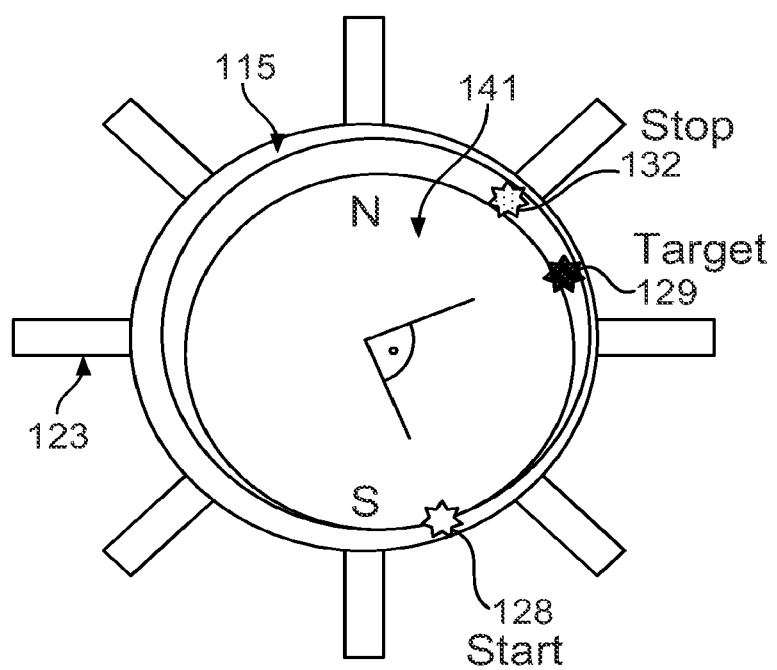
FIG. 8 describes a procedure for rolling a magnet of a rotor along a stator of an implantable blood pump.

FIG. 8 describes a procedure for rolling the permanent magnet 141 of the rotor 140 along the stator 120 or the wall 115 of the implantable blood pump 100. In particular, FIG. 8 illustrates the case where neither of the magnetic poles of the magnet 141 is contacting the wall 115 or the stator 120 before the start-up procedure at the start point 128. A computer-implemented start-up algorithm may compute a target point 129 which might not be the optimum position for a start-up position with reduced current demand, because due to an eccentricity of the pump assembly, the start point 128 is not at one of the magnetic poles (north or south pole) of the magnet 141. This may lead to an unfavorable end position calculated based on the start point 128 of the magnet 141 after the rolling phase is completed. An actual optimum stop position 132 for a rotation preceding a take-off may in this regard deviate from the calculated target position 129 in this case. In some situations the eccentricity of the pump assembly may lead to a restoring of the initial position of the magnet 141 within the pump 100, e.g. the magnet 141 may become stuck after the rolling at the same position with respect to the wall 115 or the stator 120 as before the rolling.

In an aspect, the current needed for the rolling phase is based on the displacement of the rotor from a center of the stator 120. For example, the target position 129 may be based on the rotor displacement. For instance, a decision if a levitation of the rotor 140 is successful or failed is made 100 milliseconds after a take-off was initiated. For example, a rotor acceleration may be started about 100 milliseconds after it was found that the levitation of the rotor is successful.

FIG. 8 describes a computer-implemented start-up procedure where no initial rotation of the rotor 140 is performed and wherein the current consumed for the rolling may be based on the rotor displacement from the center of the stator. If the start-up (e.g. the take-off) was not successful, the start-up procedure is repeated by performing the waiting phase, the rolling phase and the take-off attempt again one or more times. The start-up procedure may take account for the situation that the magnet 141 touches the wall 115 with a part of the magnet 141 that is different from the magnetic poles of the magnet 141. This may allow to determine a stop position 132, wherein the rotor touching the wall 115 at the stop position 132 experiences less magnetic attraction (e.g., by the stator 120) compared to the rotor touching the wall 115 at the target position 129.

Figure 9:
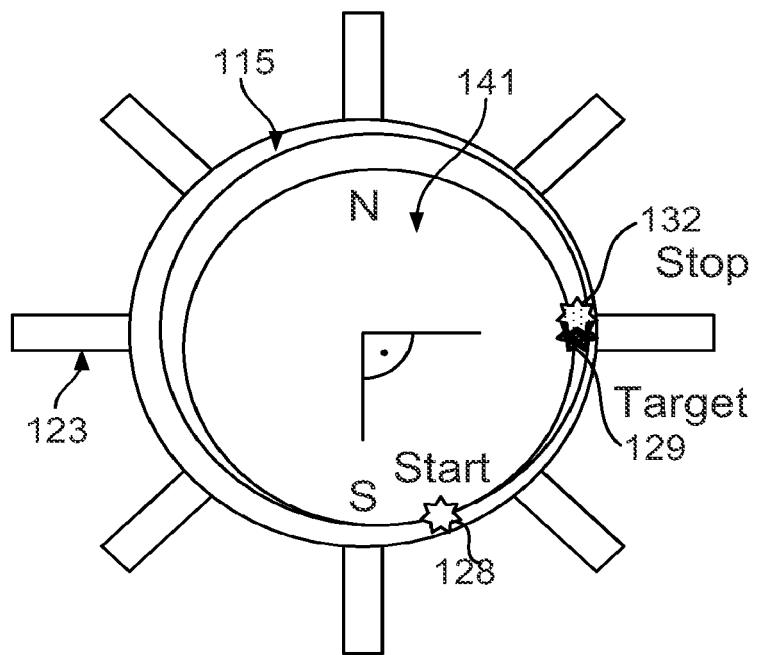
FIG. 9 describes a procedure for combining rotating and rolling a magnet of a rotor in an implantable blood pump.
Figure 9:
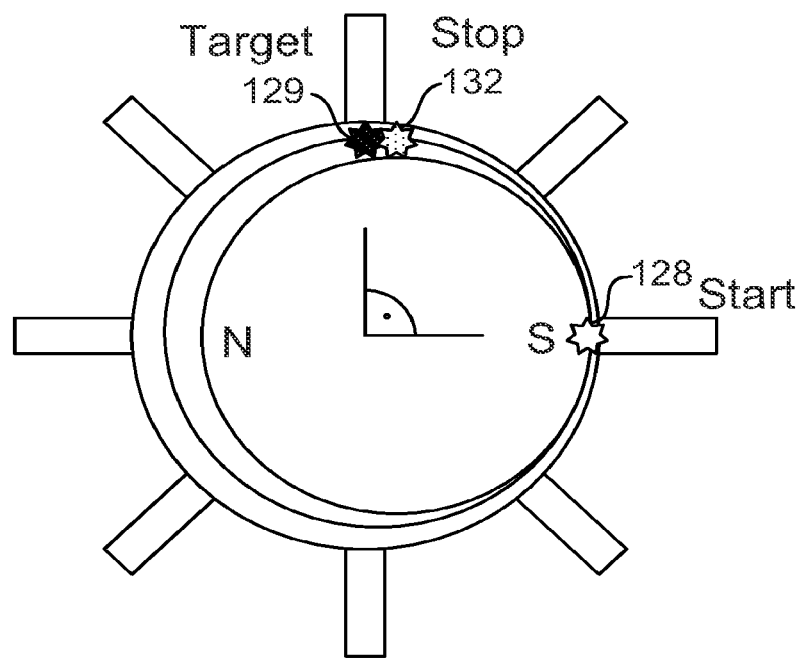

FIG. 9 describes a computer-implemented method for combining rotating and rolling a magnet 141 of a rotor 140 in an implantable blood pump 100. In this optimized start-up algorithm, an initial rotation of the rotor 140 is performed before a rolling of the rotor 140 or the magnet 141 is executed. In an aspect, the rotor 140 is rotated by an angle of between 45 and 270 degrees, preferentially by an angle of 90 degrees. In an aspect, the rotor 140 is initially rotated by an angle equal or approximate to 360 degrees divided by twice the number of magnetic poles that the magnet 141 of the rotor 140 possesses. For example, in case the magnet 141 possesses four magnetic poles (e.g., two magnetic pole pairs), the rotor 140 may be initially rotated by an angle of about 45 degrees. In an aspect, the current consumed for the rolling following the initial rotation is constant. For example the current consumed for the rolling is less than about 2 ampere. In an aspect, the target position 129 is based on the displacement of the rotor 140 with respect to a center of the stator 120 and based on an angular position of the rotor 140 or of the magnetic orientation of the magnet 141.

In a general aspect of the optimized start-up algorithm, before the rolling, the initial rotation of the rotor 140 is performed by which the rotor 140 is rotated. This may prevent the magnet 141 of the rotor 140 from becoming stuck at a position within the pump 100, e.g. a position from which a probability of a start-up and/or a take-off may be not high enough for a reliable operation of the pump 100 or, e.g. the position may be a position at which a current needed for a take-off may be exceeding 5 ampere. This may be a mitigation for the reset of the power supply and/or digital signal processing due to a voltage drop reducing take-off currents exceeding 5 ampere driven through high eccentricity and non-optimal rotor start positions 128.

This optimized start-up algorithm may allow the rotor 140 to rotate and to move to a new position, even if a reset of the power supply, the electronics or the digital signal processing happens during the take-off attempt of the start-up algorithm. This particular aspect described herein may allow use of less start-up current, e.g. less peak current during the take-off attempt of the start-up. By initially rotating the rotor 140, subsequent take-off attempts are performed starting from different physical locations within the pump 100. It can thus be achieved that the rotor 140 does not get stuck at the same position during subsequent take-off attempts. The rotation of the rotor 140 (e.g., before performing the rolling of the rotor 140) may lead after the rotation to a different direction of the magnetic attraction force between the magnet 141 and the stator 120 compared to before the rotation. In an aspect, the rotation of the rotor (e.g., before performing the rolling of the rotor) may lead after the rotation to a different (e.g., reduced) absolute magnitude of the magnetic attraction force between the magnet 141 and the stator 120 compared to before the rotation.

FIG. 9 illustrates an example of the optimized start-up algorithm. The optimized start-up algorithm described herein may take into account that the start position 128, e.g. the initial point in which the magnet 141 touches the wall 115 or the stator 120, may not be equal with either of one of the two magnetic poles of the magnet 141 of the rotor 140. If none of the poles of the magnet 141 of the rotor 140 falls on the start position 128 (e.g., if the eccentricity leads to a contact between a fraction of the magnet 141, that is not a part of one of the poles, and the wall 115), the rotation of the rotor 140 is applied to the rotor 140 before a rolling of the magnet 141 is subsequently performed. For example, the optimized start-up algorithm computes the target position 129 of the rolling taking into account the rotor displacement from the center of the stator 120 (or the flow conduit 103) and the angular position of the rotor 140 (e.g. the orientation of the magnetic moment of the magnet 141). By using this information, the computed target position 129 of the rolling may match the optimum stop position 132 for the rolling. A rolling step may place the magnet 141 in a position where the current for the take-off may be minimized, e.g. may be reduced to below 5 ampère. For example, the take-off position resulting after rolling (e.g. the target position 129) may represent a position at which the magnet 141 of the rotor 140 experiences reduced magnetic attraction compared to a take-off position at the start position 128.

The particular implementation or aspect described herein may ensure different start positions (e.g., take-off positions or positions for attempts to start the pump 100) between subsequent start-up procedures. These different take-off or start positions 128 in subsequent start-up procedures may be associated with different environmental conditions for the rotor 140. For example, one or more of the parameters magnetic field surrounding the rotor 140, eccentricity, roughness of the wall 115, magnetic fields leaving the pole pieces 123a-f and rotor tilt may be different.

Figure 10:
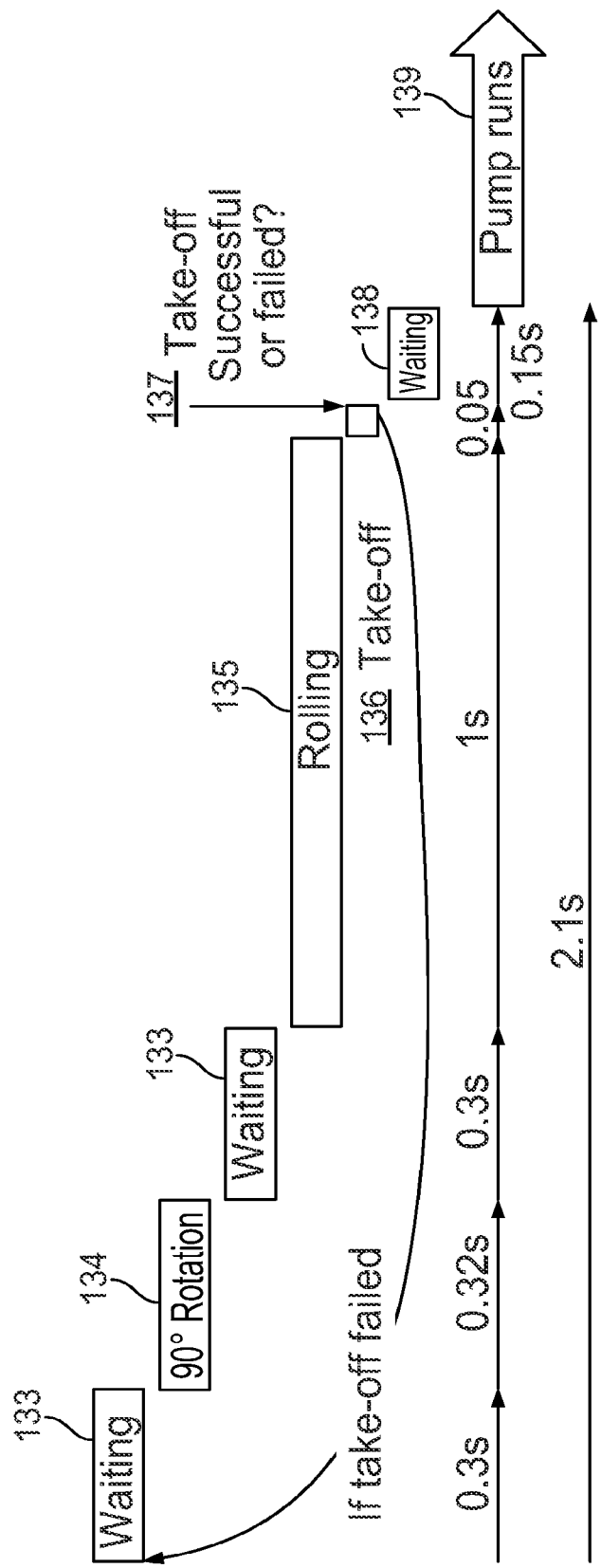
FIG. 10 describes a flow chart for exemplary procedural steps in a start-up algorithm according to FIG. 9.

FIG. 10 describes a flow chart for exemplary procedural steps in the optimized start-up algorithm according to FIG. 9. The optimized start-up algorithm may be a computer-implemented method, wherein a processor of the computer executes one or more of the following procedural steps. The start-up algorithm may start with an initial waiting phase 133 lasting a waiting time duration. For example, the waiting time duration may be 0.3 seconds long. The waiting phase may be followed by a rotation 134 of the rotor 140. In an aspect, the rotor 140 is rotated by an angle equal or approximate to 360 degrees divided by twice the number of magnetic poles that the magnet 141 of the rotor 140 possesses. For example, the rotor 140 may be rotated by an angle of about 90 degrees. The rotation may be followed by a further waiting phase 133. The rotation may take 0.32 seconds and the further waiting phase may last for 0.3 seconds. Following the further waiting phase 133, a rolling 135 of the rotor 140 or the magnet 141 is performed. During the initial waiting phase or after the rotation, the computer-implemented method computes a target position 129, to which the magnet 141 or the rotor 140 is rolled to. The target position 129 may represent a position at which the magnet 141 of the rotor 140 experiences reduced magnetic attraction forces compared to the situation before the rolling. The rolling may take 1 second. During the rolling phase, the permanent magnet 141 of the rotor 140 may be aligned in such a way that the equator of the magnet 141 faces or touches the target position 129, or the equator is touching the wall 115 at a proximity of one of the pole pieces 123a-f of the stator 120 after the rolling. This may lead to a reduced magnetic attracting force between the magnet 141 and the stator 120 after the rolling compared to before the rolling. Subsequent to the arrival of the magnet 141 or the rotor 140 at the target position 129, a take-off 136 attempt is performed, where the rotor 140 is attempted to be released from the wall 115 or the stator 120. The Hall sensor 129 according to one or more aspects described above may provide a voltage output that allows the determination of whether the take-off was successful or if the take-off failed. The take-off 136 is classified 137 as successful, if the rotor 140 may be levitated and/or may be started to rotate at the nominal rotation speed for an operation of the implantable blood pump 100. For example, the take-off 136 may be classified 137 as successful, if, after the take-off, the rotor 140 may be located within a predefined geometric volume of the pump 100.

The take-off 136 is classified 137 as failed if the magnet 141 or the rotor 140 remains contacting or touching the wall 115 or one or more pole pieces 123 of the stator 120. For example, the take-off 136 is determined 137 to have failed if the magnet 141 or the rotor 140 is falling back to the target position 129 or if the magnet 141 remains magnetically attracted by the wall 115 or the stator 120. For example, the take-off 136 may be classified 137 as failed, if, after the take-off, the rotor 140 may not be located within a predefined geometric volume of the pump. For example, the rotor 140 may not start rotating at a nominal rotation speed for pumping blood through the pump, if the rotor 140 is located outside the predetermined geometric volume of the pump 100. In an aspect, the take-off 136 may take 0.05 seconds. If the take-off 136 is determined 137 as failed, then the start-up algorithm starts again from the beginning. The repeated rotation 134 of the rotor 140, e.g. by 90 degrees, may ensure different start positions between subsequent start-up procedures (e.g., between subsequent take-off 136 attempts or attempts to start the pump 100). These different start positions 128 due to the rotation 134 of the rotor 140 before the rolling 135 in subsequent start-up attempts may be associated with different environmental conditions of the rotor at the beginning of the start-up attempts.

An additional waiting phase 138 follows a successful take-off, wherein the waiting phase 138 may last for 0.15 seconds. The total time required for the optimized start-up algorithm before the rotor is entering an accelerating phase 139 may be 2.1 seconds. In the accelerating phase 139, the rotor 140 may be accelerated to the nominal rotation speed required for an operation of the implantable blood pump, i.e. for the pump to be able to pump blood. The peak current needed for the accelerating phase may be less than the peak current needed for the take-off. The peak current needed for the take-off may be less than about 5 ampère. Optionally, before the initial waiting phase starts, an additional time window of maximal 2 seconds may be present during which a command is sent to the control electronics 130, wherein the command is configured to enable or disable the optimized start-up algorithm.

The particular aspects or implementations of the optimized start-up algorithm described in FIGS. 9 and 10 may provide a couple of advantages. First, a current consumption of an implantable blood pump may be reduced. A peak current demanded by a start-up of an implantable blood pump may be reduced. This may prevent a reset of a power supply of an implantable blood pump due to an overload. For example, a peak current of less than 5 ampère may be achieved for the start-up. Second, a current needed to perform a rolling of a magnet of a rotor of an implantable blood pump may be reduced. For example, a current of less than 2 ampere may be achieved for the rolling of the magnet. Third, improved positions for a successful start-up of the rotor may be provided for the magnet of the rotor. For example, no later than a second try of the start-up may be successful. Fourth, a time duration needed for a successful start-up of a rotor of an implantable blood pump may be reduced. For example, the time duration may be reduced to less than 3 seconds. Fifth, a compact, lightweight power supply may be sufficient to provide the peak current required for the optimized start-up algorithm. Sixth, larger deviations for the production of the components in the pump may be tolerated. For example, the larger production tolerances regarding eccentricity may be acceptable due to the optimized start-up algorithm. Generally, the inventions described herein meet the continuing need for improved power efficiency. A reduction in the peak current demand and/or power usage may enable use of a smaller power source and/or motor, which can be important for implantable devices where form factor influences surgical techniques and options for implantation locations. Likewise, increased power efficiency may extend the time the pump can be operated using a rechargeable power source.

Figure 11:
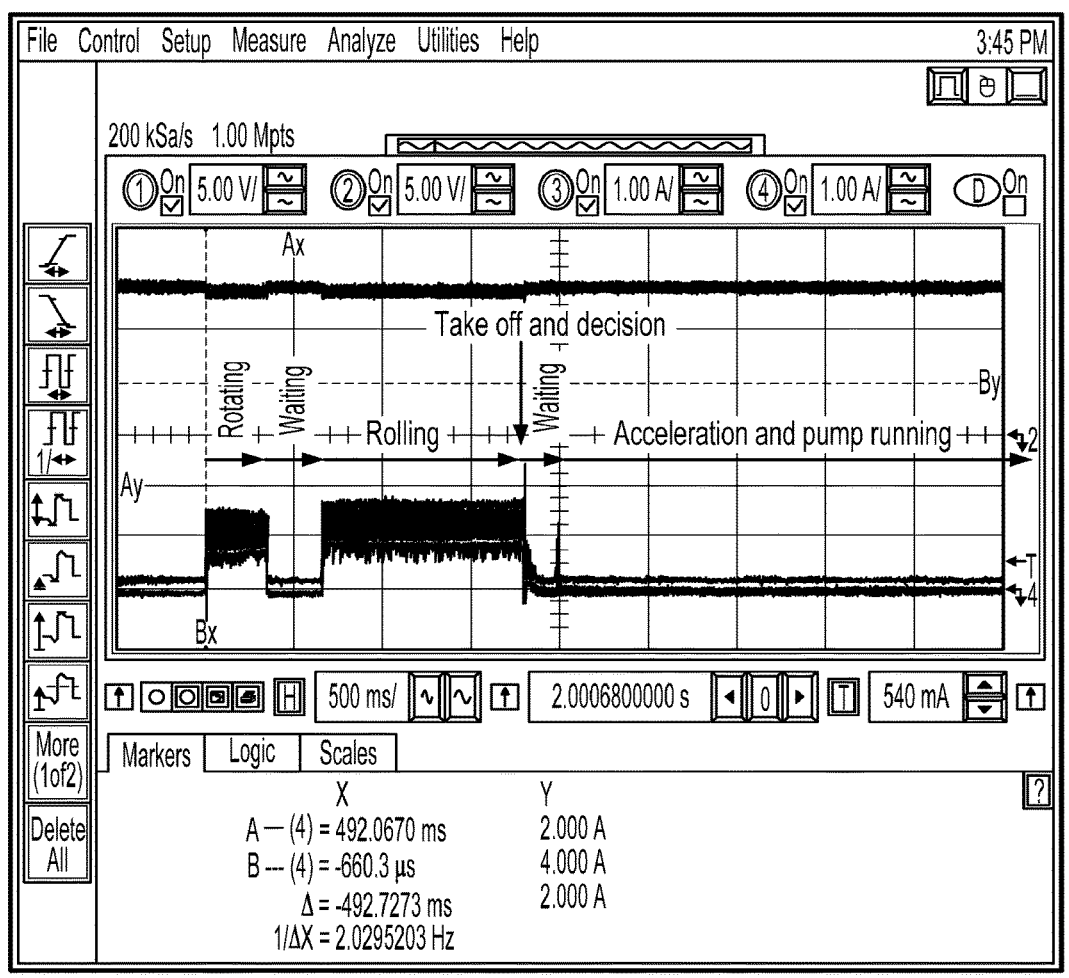
FIG. 11 describes exemplary results of a current consumption of the start-up algorithm according to FIGS. 9 and 10.

FIG. 11 describes exemplary results of a current consumption of the optimized start-up algorithm according to FIGS. 9 and 10. In this example, a second take-off is classified as successful. FIG. 11 illustrates a sequence according to one or more aspects of the optimized start-up algorithm described herein. The algorithm includes rotating the rotor by 90 degrees, waiting, rolling the rotor or magnet to a computed target position 129, performing a first take-off attempt, determine if the first take-off attempt was successful, waiting, if and only if the first take-off was not successful perform a second rotating of the rotor by 90 degrees followed by waiting, rolling of the magnet or the rotor, performing a second take-off attempt, determine if the second take-off attempt was successful, waiting and subsequently accelerating the rotor and running the implantable blood pump 100. In an aspect, the time needed to accelerate the rotator to the nominal rotation speed for an operation of the pump may be less than 1 second after the beginning of the acceleration phase. In an aspect, the current applied or consumed for the rolling is constant, e.g. the current may be less than about 2 ampere. In an aspect, the time for performing the determining if the take-off was successfully is less than 100 milliseconds, preferentially be 50 milliseconds.

In a general aspect, for determining if the take-off was successful, the output voltage provided by the Hall sensor as described above may allow to determine (e.g., classify) if the magnet 141 is located within a predefined geometric volume within the flow conduit 103. If and only if the magnet 141 is determined to be within this geometric volume, then the take-off is classified to be successful. If the magnet 141 is not located within the geometric area, then the take-off is classified as failed or not successful.

A number of implementations have been described. Nevertheless, it will be understood that various modifications may be made without departing from the spirit and scope of the claimed invention. For example, the cap 118 can be engaged with the peripheral wall 116 using a different attachment mechanism or technique, including snap-fit engagement, adhesives, or welding. Additionally, while the cap 118 has been described as defining the outlet opening 105 and the chamfered edge 114, the outlet opening 105 and/or the chamfered edge 114 can be defined by the peripheral wall 116 or by both the peripheral wall 116 and the cap 118. Similarly, the dividing wall 115 can be formed as part of the cap 118.

Additionally, the rotor 140 can include two or more permanent magnets. The number and configuration of the pole pieces 123 can also be varied. The operation of the control electronics 130 is selected to account for the number and position of pole pieces of the stator and permanent magnets of the rotor. Also, the cap 118 can be engaged with the peripheral wall using other techniques, such as adhesives, welding, snap-fit, shrink-fit, or other technique or structure. Similarly, the first face 111 may be formed from a separate piece of material than the peripheral wall 116 and the first face 111, including the inlet cannula 112, can be attached to the peripheral wall 116, such as by welding, after the control electronics 130 and the stator 120 have been mounted in the internal compartment 117. The shroud 145 may be omitted and optionally replaced by other flow control devices to achieve a desired pump efficiency. As another option, the control electronics 130 can be located external to the pump 100, such as in a separate housing implanted in the patient's abdomen, or external to the patient's body.

In some implementations, the dimensions of the housing 110 can be larger or smaller than those described above. Similarly, the ratio of the width W of the housing 110 to the thickness T of the housing can be different than the ratio described above. For example, the width W can be from about 1.1 to about 5 times greater than the thickness T. Additionally, the permanent magnet 141 of the rotor 140 can include two or more pairs of north and south magnetic poles. While the peripheral wall 116 and the dividing wall 115 are illustrated as cylinders having circular cross-sectional shapes, one or both can alternatively be formed having other cross-sectional shapes, such as oval, or an irregular shape. Similarly, the peripheral wall 116 can be tapered such that the housing does not have a constant width W from the first face 111 to the second face 113.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis, such as where the patient's aortic valve is surgically sealed. In a particular aspect described herein, the Hall sensor may allow the system to monitor the position of the rotor of the pump 100 and may thereby help to ensure a proper operating status of the implantable blood pump 100.

As used in the present disclosure, the term "computer" is intended to encompass any suitable processing device.

Regardless of the particular implementation, "procedure" or "algorithm" may include computer-readable instructions, firmware, wired or programmed hardware, or any combination thereof on a tangible and non-transitory medium operable when executed to perform at least the processes and operations described herein. Indeed, each procedure or algorithm component may be fully or partially written or described in any appropriate computer language including C, C++, Java, Visual Basic, assembler, Perl, any suitable version of 4GL, as well as others. One of skill will appreciate that the algorithm may be implemented on several controller components. In various embodiments, the "controller" includes one or more electronics inside the patient's body and/or external the body.

The figures and accompanying description illustrate example processes and computer-implementable techniques. It will be understood that the processes are for illustration purposes only and that the described or similar techniques may be performed at any appropriate time, including concurrently, individually, or in combination. In addition, many of the steps in these processes may take place simultaneously, concurrently, and/or in different orders or combinations than shown.

Thus, particular aspects of the subject-matter have been described. Other aspects or embodiments are within the scope of the following claims. In some cases, the actions recited in the claims can be performed in a different order or combination and still achieve desirable results. In certain aspects, multitasking and parallel processing may be advantageous.

In other words, although this disclosure has been described in terms of certain implementations and aspects, generally associated methods, alterations and permutations of these implementations and methods will be apparent to those skilled in the art. Accordingly, the above description of example implementations does not define or constrain this disclosure. Other changes, substitutions and alterations are also possible without departing from the spirit and scope of this disclosure.

Aspects of the subject-matter and the operations described in this specification can be implemented in digital electronic circuitry, or in computer software, firmware, or hardware, including the structures disclosed in this specification and their structural equivalents, or in combinations of one or more of them. Embodiments of the subject-matter described in this specification can be implemented as one or more computer programs, i.e., one or more modules of computer program instructions, encoded on computer storage medium for execution by, or to control the operation of a data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "computer", "server", "processor" or "processing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and operating environment can realize various different computing model infrastructures.

A computer algorithm (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer may be a processor for performing actions in accordance with instructions and one or more memory devices for storing instructions and data. Generally, a computer or computing device 200 will also include, or be operatively coupled to receive data from or transfer data to, or both, one or more mass storage devices for storing data, e.g., magnetic, magneto-optical disks, or optical disks. However, a computer or computing device need not have such devices. Moreover, a computer or computing device can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject-matter described in this specification can be implemented on a computer having a non-flexible or flexible screen 201, e.g., a CRT (cathode ray tube), LCD (liquid crystal display) or OLED (organic light emitting diode) monitor, for displaying information to the user and a keyboard and a pointer 205, e.g., a finger, a stylus, a mouse or a trackball, by which the user can provide input to the computer. Other kinds of devices can be used to provide for interaction with a user as well; for example, feedback provided to the user can be any form of sensory feedback, e.g., touch feedback, visual feedback, auditory feedback, or tactile feedback; and input from the user can be received in any form, including acoustic, speech, touch or tactile input. In addition, a computer can interact with a user by sending documents to and receiving documents from a device that is used by the user; for example, by sending web pages to a web browser on a user's user device in response to requests received from the web browser.

Embodiments of the subject-matter described in this specification can be implemented in a computing system that includes a back-end component, e.g., as a server 300, or that includes a middleware component, e.g., an application server, or that includes a front-end component, e.g., a user computer having a graphical user interface or a Web browser through which a user can interact with an implementation of the subject-matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In general, the separation of various system components in the aspects described above should not be understood as requiring such separation in all implementations, and it should be understood that the described program components and system components can generally be integrated together in a single software or hardware product or packaged into multiple software or hardware products.

The preceding figures and accompanying description illustrate example processes and example devices. But example components contemplate using, implementing, or executing any suitable technique for performing these and other tasks. It will be understood that these processes and parts are for illustration purposes only and that the described or similar techniques may be performed at any appropriate time, including concurrently, individually, in parallel, and/or in combination. In addition, many of the steps or parts in these processes may take place simultaneously, concurrently, in parallel, and/or in different orders than as shown. Moreover, components with additional parts, fewer parts, and/or different parts, may be used so long as the devices remain appropriate. Moreover, although features may be described above as acting in certain combinations and even initially claimed as such, one or more features from a claimed combination can in some cases be excised from the combination, and the claimed combination may be directed to a sub-combination or variation of a sub-combination.

In other words, although this disclosure has been described in terms of certain aspects, implementations, examples or generally associated methods, alterations and permutations of these aspects, implementations or methods will be apparent to those skilled in the art. Accordingly, the above description of example aspects, implementations or embodiments do not define or constrain this disclosure. Other changes, substitutions, and alterations are also possible without departing from the spirit and scope of this disclosure.

What is claimed is:

1. A method for starting a rotor of an implantable blood pump, the method comprising:
    performing an initial rotation of the rotor by an angle larger than an angle corresponding to a quarter of an angular distance between two neighboring magnetic poles of the rotor; and
    after the performing, rolling the rotor, while the rotor remains in contact with a dividing wall defining a blood flow conduit in which the rotor is disposed, from a first start position to a first target position prior to magnetic levitation of the rotor to position the rotor within the blood flow conduit for pumping blood, wherein a magnet of the rotor experiences a reduced magnetic attraction at the first target position compared to the first start position.

2. The method of claim 1, wherein the angle of the rotation is about half of the angular distance between two neighboring magnetic poles of the rotor or a multiple thereof.

3. The method of claim 1, wherein the angle of the initial rotation is between about 45 and about 270 degrees.

4. The method of claim 1, wherein the angle of the initial rotation is about 90 degrees.

5. The method of claim 1, further comprising:
    determining a current position of the rotor by using one or more Hall sensors;
    performing a take-off operation attempting to move the rotor into the predefined geometric volume; and
    determining if the rotor is positioned within the predefined geometric volume after performing the take-off operation.

6. The method of claim 5, further comprising:
    determining if the rotor is positioned within the predefined geometric volume, and if the rotor is not positioned within the predefined geometric volume, performing the additional operations of:
    performing a second rotation of the rotor corresponding substantially to an angle of twice the interval between two neighboring pole pieces of a stator of the implantable blood pump;
    rolling the rotor from a second start position to a second target position, wherein the magnet of the rotor experiences a reduced magnetic attraction at the second target position compared to the second start position; and
    performing a second take-off operation attempting to move the rotor into the predefined geometric volume.

7. A method comprising:
    performing a rotation of a rotor of an implantable blood pump, the rotation of the rotor moving the rotor from a first position to a second position;
    after performing the rotation of the rotor, waiting for a period of time with the rotor in the second position; and
    after waiting for the period of time with the rotor in the second position, rolling the rotor from the second position to a take-off position for moving the rotor into a predefined geometric volume.

8. The method of claim 7, further comprising determining that a rotor of an implantable is not positioned within a predefined geometric volume of the blood pump; and
    wherein performing the rotation of the rotor occurs in response to determining that the rotor is not positioned within the predefined geometric volume.

9. The method of claim 7, further comprising determining a target position of the rotor with respect to a stator of the implantable blood pump;
    wherein rolling the rotor from the second position to the take-off position comprises rolling the rotor to the target position.

10. The method of claim 8, further comprising, after rolling the rotor to the take-off position, performing a take-off operation attempting to move the rotor into the predefined geometric volume.

* * * * *